United States Patent [19]
Blanke et al.

[11] 4,030,349
[45] June 21, 1977

[54] ENGINE ANALYSIS APPARATUS

[75] Inventors: John David Blanke, Fullerton; Norman Eliot Brunell, Sherman Oaks, both of Calif.

[73] Assignee: Beckman Instruments, Inc., Fullerton, Calif.

[22] Filed: Aug. 16, 1976

[21] Appl. No.: 714,144

[52] U.S. Cl. .................................. 73/116; 73/23
[51] Int. Cl.² .................................. G01M 15/00
[58] Field of Search ........... 73/116, 23, 117.3, 117; 23/288 F, 232 E; 60/277

[56] References Cited
UNITED STATES PATENTS

| | | | |
|---|---|---|---|
| 3,938,479 | 2/1976 | Oberstadt | 73/116 X |
| 3,969,932 | 7/1976 | Rieger et al. | 73/118 |

*Primary Examiner*—Jerry W. Myracle
*Attorney, Agent, or Firm*—R. J. Steinmeyer; P. R. Harder; D. A. Streck

[57] ABSTRACT

Exhaust gas diagnostic apparatus capable of use on both catalytic converter equipped and non-catalytic converter equipped motor vehicles is disclosed. A fast response oxygen analyzer is coupled with means for differentiating the signal output of the oxygen analyzer. In this manner, both the quantity and rate of change of oxygen in the exhaust gas is made available to apparatus included therein for indicating and/or alarming quantity and rate of change values outside preset limits. The apparatus is particularly directed to the detection of an engine misfire condition. The apparatus disclosed permits diagnosing problems without disconnecting the air injector system (if present) or having a port prior to the catalytic converter. As it alarms on transients, it is independent of the steady state oxygen level.

10 Claims, 5 Drawing Figures

ENGINE ANALYSIS APPARATUS

BACKGROUND OF THE INVENTION

Control of emissions from motor vehicles is now an accepted and necessary automotive design consideration throughout the world. In the United States since about 1965 (and earlier in California) all motor vehicles sold have incorporated some form of emission control. Recently, more vehicles sold for use in countries other than the United States have also been designed to reduce pollutants. The speed with which engine design changes have taken place to satisfy pollution reduction requirements has been extraordinary. Not only have the engine and vehicle manufacturers had to engage in major expenditures for facilities, equipment and accelerated technical achievement, but similarly, the automotive service industry has been experiencing a major upheaval in the effort to provide continuing qualified engine malfunction diagnosis and maintenance capability.

Exhaust emission standards in the United States have become increasingly stringent. Concurrent with the emphasis on reducing emissions, the automotive service industry throughout the world was beginning to acquire exhaust analyzers for measurement of hydrocarbons (HC) and/or carbon monoxide (CO). Now, the majority of qualified automobile service centers, particularly in the United States, use HC/CO analyzers routinely as an important diagnostic aid and also to inspect or verify vehicle manufacturer specifications at idle. In a number of areas within the United States, legislation requires service garages to have an approved HC/CO analyzer. CO analyzers have also become a mandatory part of emission conrols programs in a number of countries other than the United States.

Service facilities have found emission analyzers a useful diagnostic/service device during routine service inspection. For example, the use of a CO analyzer for properly adjusting carburetor balance and air/fuel ratios is now standard practice. Hydrocarbon measurements as an indication of ignition problems, a malfunctioning exhaust or intake valve, etc., is also widely used as a quick method of screening vehicles for further diagnosis by conventional oscilloscope testers.

The stringent standards in the United States for 1975 have forced most automobile manufacturers to use catalytic converters on current production vehicles to provide adequate control of exhaust emissions of hydrocarbons and carbon monoxide. Unfortunately, the effective use of HC/CO exhaust gas analyzers as a diagnostic aid for vehicles equipped with catalytic converters is more complicated than for vehicles without converters. In fact, if the converter is working properly, engine diagnosis with HC/CO analyzers is extremely difficult unless the vehicle has an exhaust sampling port ahead of the converter. When the catalytic converter is functioning properly, it oxidizes essentially all of the HC and CO to $CO_2$ and water vapor. Consequently, the concentrations in the exhaust are so low they cannot be measured with accuracy with existing "garage-type" instrumentation. The changes in raw exhaust concentrations of HC, for example, as a result of intermittent misfire or "lean roll", no longer appear in the converted exhaust gases and the conventional exhaust gas analyzer loses value as a diagnostic tool.

The detection of a lean roll condition is becoming of great concern not only to the service garage owner doing after sale service, but, to the automobile manufacturer and his dealers as well. The leaner the mixture at which the carburetor is set, the greater the economy when the engine is operating in the manner for which it was designed. A slight deviation, however, can put the engine in a lean roll condition which increases both gasoline consumption and the emission of pollutants at the exhaust. The phenomenon of lean roll can best be understood with reference to FIG. 1. In a typical engine 10 having cylinders 12, a common intake manifold 14 is connected from a carburetor 16 to the intake ports 18 of cylinders 12. Obviously, the distance from the two outside cylinders 12 is greater than the distance to the two inside cylinders 12. The variation in the distances that the gasoline/air mixture must travel through the manifold 14 to reach the various cylinders 12 causes a difference in the mixture at the various cylinders 12 even though produced by a common carburetor 16. The mixture at the inner cylinders 12 tends to be richer than the mixture at the outer cylinders 12. In order to ignite and burn properly in the cylinders 12 the gasoline to air ratio of the fuel mixture must be within certain high and low limits. As the mixture is made more lean (less gasoline to a fixed volume of air) a point will be reached where the mixtue will not ignite.

Since, as stated earlier, the mixture at the two outer cylinders 12 tends to be leaner, as the mixture at the carburetor 16 is adjusted leaner, the two outer cylinders 12 will reach a point where they cyclically begin to misfire. This is called the lean-roll condition. As the mixture received drops below the critical level, the outer cylinders 12 misfire. This condition can occur individually or simultaneously as the exact mixture in any cylinder 12 at any instant is a function of many factors including the mixture at the carburetor at that instant (which may vary), the temperature of the manifold 14, whether the cylinder 12 fired on the last power cycle, and the amount of dilutants retained from the exhaust cycle during the intake stroke. Lean mixture can, of course, occur at all the cylinders 12 but we are concerned here with the slow roll phenomenon which is more correlatable to the outside cylinders (those furthest from the carburetor) in any engine.

Excess $O_2$ in the exhaust gas of vehicles with catalytic converters has recently been identified as a major cause of increased sulfate emissions. It is known, that sulfates in high enough concentrations are injurious to health, and standards for their control in vehicle exhaust are being prepared in the United States. The net effect of this action will have a bearing on the automotive service industry. $O_2$ concentrations and the source of $O_2$ in the exhaust gas (i.e., from secondary air pumps or through modulated air bleeds to the induction system) will become an important control and adjustment parameter in the design as well as in the proper servicing of vehicles in subsequent years. Primarily because of the sulfate issue, it is expected that automotive engineers will no longer be able to use air pumps to deliver more air than necessary for efficient catalytic conversion. The service mechanic will be required to make precise adjustments of air control devices based on exhaust concentrations of $O_2$. Of course, the measurement of HC and CO will continue to be important tools as well, in the complete diagnosis of engines and emission control systems.

In addition to reactor or converter equipped engines, 1975 saw the introduction of stratified charge engines as effective approaches to reach the present stringent exhaust emission standards. Several manufacturers incorporated "lean-burn" (available oxygen in excess of that required for stoichiometry) during at least some engine operating modes. Especially from a drivability point of view, these engines will require critical air-fuel ratio adjustments.

In considering the environment wherein the present invention is employed, the term "reactor" is used in a generic sense. Actually, reactor equipped vehicles can include thermal reactors, catalytic converters, manifold reactors or combinations of these. In a broad sense, they are similar in that they all need oxygen in excess of that required for normal combustion in the engine to work effectively.

Thermal reactors are simply insulated post-combustion chambers located in the vehicle exhaust manifolds. They burn combustibles under relatively low pressure conditions. To function effectively, they must be kept hot. Efficient combustion requires accurate control of secondary air rates and usually the basic engine must be adjusted on the rich side to provide adequate fuel value. Most thermal reactors utilize a separate ignition source (spark plug) to initiate and promulgate combustion.

Catalytic converters also must operate at relatively high temperatures (450°–700° C) to accomplish efficient conversion of HC and CO and $CO_2$ and $H_2O$. Through 1977 it is expected that all catalytic converter vehicles will utilize oxidizing catalysts (rather than reduction catalysts) which require free $O_2$ to function. The catalyst, which may be either in the pellet or monolithic form, is usually a substrate of alumina or similar material coated with a small amount of platinum and/or palladium. The noble metal catalyzes an oxidation reaction in the presence of HC, CO and $O_2$ to accomplish coversion to non-toxic products of complete combustion. The reactions are:

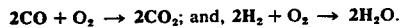

$$2CO + O_2 \rightarrow 2CO_2; \text{ and, } 2H_2 + O_2 \rightarrow 2H_2O.$$

If there is not enough $O_2$ available, conversion efficiency suffers and, if there is an excess of $O_2$ available, the catalyst assists in the conversion of gasoline sulfur to undesirable $SO_3$ which ultimately forms $H_2SO_4$ and other sulfates. The problem of the production of $H_2SO_4$ by catalytic converter equipped automobiles is one of great concern presently under study.

Manifold reactors are similar in many respects to thermal reactors, except they do not utilize a separate ignition souce. Air is pumped into the exhaust valve port area and in combining with the high temperataure exhaust gases, oxidation continues to occur for some distance in the exhaust system. Of course, excessive air tends to squelch the combustion rates and reduce the conversion efficiency.

As the complexity of the engines has increased, so has the need for regular maintenance. In an effort to ensure regular maintenance, the U.S. Federal Government is requiring certain areas to establish periodic vehicle inspection programs. The primary objective of these programs is to bring ambient air pollution levels to federally specified levels. As the untuned vehicle is a major cause of pollution from mobile sources, these programs are designed to force a malfunctioning vehicle to obtain an engine tune-up or to remove the defective vehicle from the road. The use of a suitable HC/CO analyzer by both Government enforcement agencies and authorized service garages has been made mandatory in a large number of these inspection programs.

The current emphasis on fuel conservation in the United States has given further incentive for the expansion of these periodic inspection programs. However, as mentioned previously, the use of an HC/CO tester as a diagnostic tool on reactor equipped vehicles is now limited. The reactors, when operating properly, are so efficient that 90 to 95% of the engine's CO and HC are oxidized and are now emitted as $CO_2$ and water vapor. The indicators the tune-up technician has learned to rely upon with pre-reactor vehicles are now no longer present. If the technician has access to the exhaust system ahead of the catalytic reactor, he can still measure these indicators. However, most 1975 automobiles do not have access ahead of the reactor. Such accesses may be added in the future, but they are difficult to reach and extremely hot to handle.

The design objective to burn all of the fuel within the combustion chambers has been achieved to an amazing degree, in modern engines. However, just 1% incomplete combustion results in about 200 ppm of unburned HC in exhaust and 10% incomplete combustion, or 10% intermittent misfire results in approximately 2000 ppm unburned HC. When inadequate quantities of air are available, products of incomplete combustion such as CO and $H_2$ are formed and if excessive air is available, some $O_2$ is found in the exhaust. Uneven fuel distribution to each cylinder and mixture ratio variations from cycle to cycle within the same cylinder also account for significant quantities of unburned products in the exhaust.

Controlling air-fuel ratios within very narrow tolerances for all operating modes has become increasingly important as emission standards have tightened. Fortunately, the optimum air-fule ratio for minimum emissions (except $NO_x$) is about the same as needed for maximum fuel economy, approximately 15.0–16.0 pounds of air to one pound of fuel. Maintaining control of the air-fuel ratio and consequently optimizing combustion efficiency becomes imperative if vehicles are to meet the emission standards and simultaneously have good fuel economy. Precision measurement of combustion efficiency in some form, therefore, becomes imperative at the service level.

Therefore, it is an object of the present invention to provide improved engine exhaust apparatus capable of detecting quantities of oxygen in the exhaust gas as well as providing a means of detecting engine misfire or lean roll.

DECRIPTION OF THE DRAWINGS

DESCRIPTION OF THE PREFERRED EMBODIMENT

Figure 1:
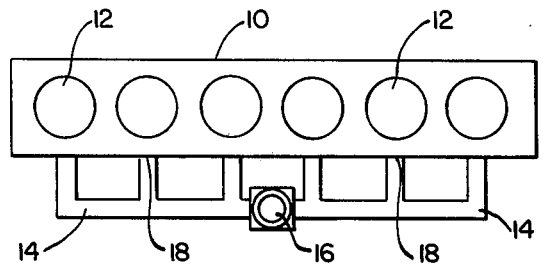
FIG. 1 is a simplified top view of an engine showing the difference in distances traveled by the fuel-air mixture between the carburetor and the various cylinders.
Figure 2:
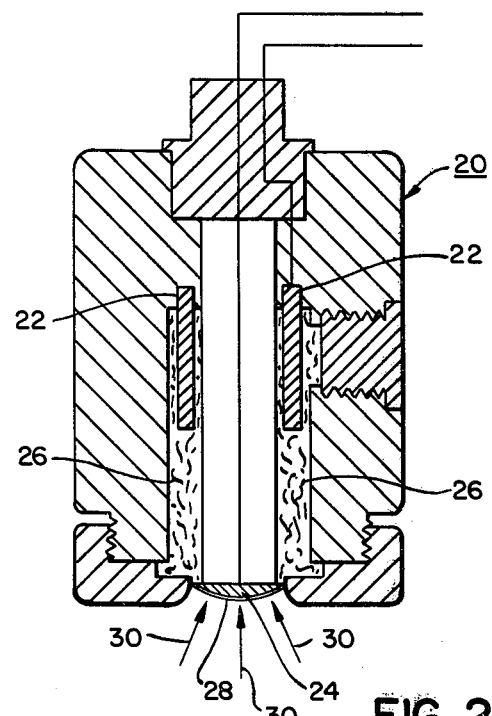
FIG. 2 is a cross-sectional elevation of a sensor for oxygen for use with the present invention.

It was found that an oxygen analyzer can be combined with the HC/CO analyzer to restore the value of exhaust gas analysis for engine diagnostic purposes since the quantity of $O_2$ is not affected by the catalytic converter. Thus, $O_2$ analysis is available whether or not the vehicle is equipped with a catalytic converter and whether or not the vehicle uses a secondary air pump. To accomplish the objectives of the present invention, it is necessary to employ a fast response oxygen analyzer (90% in five seconds or better). It is possible by techniques known in the art to provide a sensor and assoicated electronics capable of such fast response oxygen sensing. Such equipment is manufactured by the assignee of the present application and forms no part of the present invention. Basically, such analysis apparatus is simple. Of course, certain proprietary techniques allow one oxygen analyzer to operate more efficiently than another. Referring to FIG. 2, in a sensor 20 two electrodes 22 and 24 are separately mounted within a body and are electrically connected by an electrolyte 26. A constant potential is impressed across the two electrodes 22 and 24. A gas-permeable membrane 28 separates the electrodes 22 and 24 from the exhaust sample 30 and fits firmly against the cathode electrode 24. Oxygen from the sample 30 diffuses through the membrane 28 and is reduced at the cathode 24. The resultant electrical current flow between the anode electrode 22 and cathode 24 is proportional to the partial pressure of oxygen in the sample 30. The sensor 20 is placed in the exhaust stream to sense the partial pressure of oxygen. A potential of 0.725 volts DC is applied across the cathode 24 and anode 22 to make the sensor oxygen selective by techniques well known in the art. When the oxygen in the exhaust stream 30 diffuses through the membrane 28, it is reduced at the cathode 24. The reduction of oxygen results in a current flow proportional to the partial pressure of oxygen in the sample. The following reactions are considered to occur:

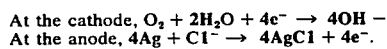

At the cathode, $O_2 + 2H_2O + 4e^- \rightarrow 4OH^-$
At the anode, $4Ag + Cl^- \rightarrow 4AgCl + 4e^-$.

When no oxygen is present, no electrical current flows in the sensor 20. When oxygen is present, electrical current flows in the sensor 20 according to the polarographic oxygen curve for the potential across the electrodes 22 and 24. The magnitude of this current is dependent upon the partial pressure of oxygen in the sample being analyzed. It should be noted that, since the sensor 20 responds to the partial pressure of oxygen, any variable that effects oxygen partial pressure must be taken into account. Two basic variables which affect partial pressure are barometric pressure and relative humidity. However, since we are measuring, in this application, at atmospheric pressure with calibration at the same pressure in relatively constant relative humidity, thesefactors have a very insignificant effect on exhaust oxygen measurements. If extremely accurate measurements are required, a correction factor can be applied.

Figure 3:
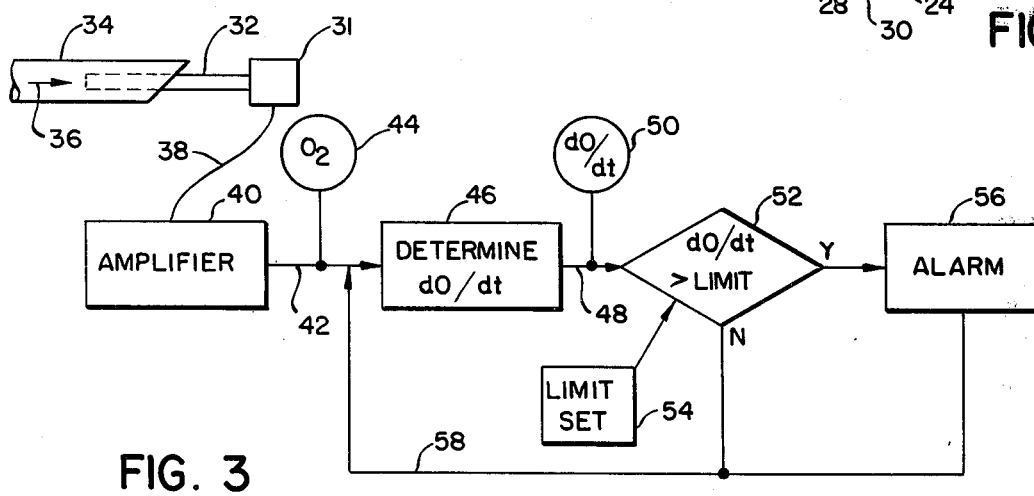
FIG. 3 is a block diagram of the apparatus comprising the present invention.

Referring now to FIG. 3, the present invention is shown employing a sensor 31 connected to a probe 32 adapted to be inserted in the exhaust pipe 34 of an automobile (not shown) and thereby conduct a portion of the exhaust gases 36 to oxygen sensor 31. Sensor 31 is connected by appropriate connection means 38 to amplifier means 40. As previously stated, sensor 31 and amplifier 40 are well known to those skilled in the art and form no part of the present invention. The only limitation on sensor 31 and amplifier 40 for proper operation of the present invention is that they behave as a fast response oxygen analyzer. That is, a change in the quantity of oxygen in exhaust gas 36 should be responded to and indicated at least to the 90% level in at least five seconds. The essential quality thus achieved is the ability to respond to changes in $O_2$ level as a result of lean-roll while rejecting short term transient spikes by this "chemical capacitor" behavior. If sensor 31 and amplifier 40 are incapable of fast response to changes in oxygen, either through damping factors or inherent design limitations, subsequent portions of the present invention will present meaningless or erroneous data to the user. The output 42 of amplifier 40, indicating the instantaneous quantity of oxygen in exhaust gas 36 as sensed by sensor 31, is connected to drive an indicating meter 44 which continuously displays the quantity of oxygen in percent in the exhaust gas 36. The output 42 of amplifier 40 is also made an input to appropriate means 46 for determining the rate of change (do/dt) of oxygen in the exhaust gases 36. d0/dt determination means 46 could be either analog or digital circuitry well known to persons skilled in the art. The output 48 of the do/dt determination means 46 is connected to do/dt indicating meter 50 for indicating the instantaneous rate of change of the oxygen content of exhaust gases 36 to the operator. Additionally, the instantaneous value of do/dt appearing at output 48 is also connected to limit comparison means 52. As with do/dt determination means 46, limit comparison means 52 could be provided by either analog or digital circuitry well known to those skilled in the art. It is preferred that limit set means 54 be provided and connected to limit comparison means 52 whereby the operator can select the limit at which the comparison will be made. Such factors as air pumping or non-air pumping and the number of cylinders in the engine may be used in determining the limit value as will be hereinafter discussed in greater detail. When the instantaneous value of do/dt is greater than the limit presently being used by limit comparison means 52, alarm 56 connected to limit comparison means 52 is activated to provide an audible and/or visible indication to the operator. In its preferred embodiment, alarm 56 is provided with adjustable means (not shown) whereby the threshold value and duration of a signal from limit comparison means 52 necessary to cause alarm 56 to activate, as well as the time duration of a signal from alarm 56 once activated, can be determined. This could be included as a factory or service type adjustment not available to the operator. It is provided so that undesired transient changes in the value of dO/dt not eliminated by the capacitive effect of the sensor 31 can be masked out and, additionally, so that in the presence of short term spikes in the value of dO/dt in which the operator may be interested, the alarm 56 will be activated for a sufficient period that the signal will be noticed by the operator. The determination of dO/dt by means 46 and the comparison against the limit by limit comparison means 52 is a constant repetitive loop function as represented by the closed loop logic line 58 from limit comparison means 52 and alarm 56.

Figure 4:
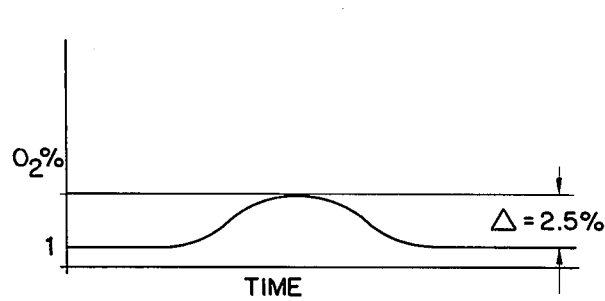
FIG. 4 is an illustration of the change in oxygen level in the exhaust of a non-airpumped engine during a lean-roll condition.
Figure 5:
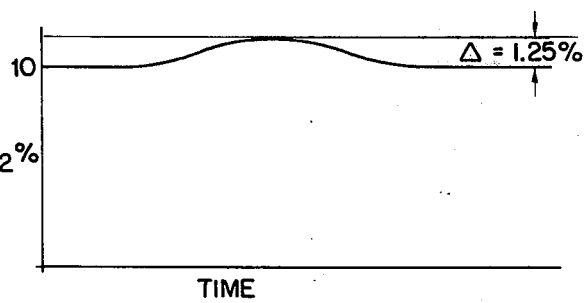
FIG. 5 is an illustration of the change in oxygen level in the exhaust of an airpumped engine during a lean-roll condition.

Referring now to FIG. 4 and FIG. 5, a further consideration in the detection of the lean roll condition is illustrated. In FIG. 4, a single lean roll increase in $O_2\%$ is shown for an engine without additional air pumping provisions. Normal atmosphere contains approximately 21% $O_2$. In an engine without additional air pumping provisions, the $O_2$ content of the exhaust gas with all cylinders firing normally is approxiamtely 1%. During a lean roll condition a spike increase in the $O_2$ level will occur in the exhaust gases over a total period of rise and fall of perhaps 10 seconds. The magnitude of the change in $O_2$ level will be according to the contribution of the non-firing cylinder to the firing cylinders in the total exhaust gas stream. In other words, the 1% $O_2$ content exhaust gases from the firing cylinders will dilute the 21% $O_2$ content exhaust gas from the non-firing cylinder on proportional basis. Thus, in an eight cylinder engine, a lean roll condition in a single cylinder will cause an increase in the $O_2$ level of the exhaust gases of about 2.5%. When the dO/dt is sensed, this will be seen as a substantial rate change.

By comparison, FIG. 5 shows the change resulting from a lean roll condition in an engine equipped with additional air pumping capability. If the same eight cylinder engine discussed above were equipped with additional air pumping means, the exhaust, when the engine was running normally, would contain approximately 7–10% $O_2$ instead of the 1% without air pumping. If, for ease of calculation, we assume the 10% $O_2$ normal state, then taking into consideration the dilution effect of the pumped air with 21% $O_2$ and the raw exhaust gases leaving the piston chamber which were indicated to be 1%, the exhaust must be approximately one-half raw exhaust gases and one-half pure air. This being the case, when the lean roll condition does occur as before, the raw exhaust gases will increase in $O_2$ content by the same 2.5%. Because of the dilution by the pumped air, however, the change in $O_2$ at the exhaust pipe will be only 1.25% with an attendant dO/dt only one-half that in the non-air pumped engine during lean roll.

It is these dilution effects of air-pumping or the like and the change in dO/dt which can be expected as a result of a lean-roll condition which determine the limit value to be used in the dO/dt-limit comparison. The greater the number of cylinders in the engine, the smaller the change in $O_2\%$ as a result of a lean-roll condition. Thus, the dO/dt value will also be less. To make the simplest system (such as that of FIG. 3 but without limit set means 54), the limit value should be chosen for the least dO/dt value which will be encountered indicating a true lean-roll condition. If the change in an eight cylinder air-blown engine is used to pick the limit value, any non-air blown engine or engine of fewer cylinders will have a dO/dt greater than the limit. In such a simplified, general purpose instrument, however, sensitivity would become a potential problem. Having set the limit at the lowest value, changes in dO/dt in non-air blown engines and engines of fewer cylinders not representing an actual lean-roll condition may, nevertheless, exceed this minimal value and signal a lean-roll condition. The limit set means 54 of FIG. 3 is provided to eliminate this problem by allowing the limit to be varied by an operator as by switches or the like as a function of such parameters as number of cylinders, air-blown/ non-air blown, etc.

As previously mentioned, the above described apparatus is primarily a misfire monitor to be used in conjunction with other calibration and test apparatus in an automotive shop or testing station. The following sequence of steps represents a typical way in which the present invention operating as a misfire monitor responding to a lean roll condition can be used in setting the idle mixture adjustment on an engine's carburetor:

a. calibrate misfire ($O_2$) monitor.

b. insert $O_2$ detecting probe in tail pipe of running vehicle.

c. adjust dwell and timing of the ignition system of the engine to within specifications and at lowest misfire rate.

d. open the idle mixture screw(s) of the carburetor in the enriching direction three turns to assure a rich mixture condition.

e. adjust one idle mixture screw leaner until the misfire monitor signals a misfire condition.

f. after the misfire signal, adjust the idle mixture screw to enrich one-half turn to provide a safety margin of richness to prevent lean roll.

h. repeat steps (e) and (f) on other idle mixture screws as required.

The above procedure is made possible by the apparatus of the present invention because the fast response oxygen analyzer sees transient conditions and a positive going oxygen spike is chemically related to an engine misfire condition. By differentiating the oxygen signal as in the present invention, the rate of change dO/dt can be related to the severity of the transient misfire condition, compared against a pre-established limit, and used to trigger an audible alarm. The alarm notifies the tune-up technician of a misfire as he is adjusting the engine, without having him look at meter slew rate to determine a misfire condition. The misfire monitor as previously described, also permits diagnosing problems without disconnecting the air injector system. As it alarms on transients, it is independent of the steady state oxygen level.

While the foregoing discussion and the preferred embodiment of the present invention is directed to the amount of oxygen and rate-of-change of oxygen in engine exhaust gases, it is to be understood that the present invention could be adapted by the use of appropriate sensors to the amount and rate-of-change of any component of the exhaust gases with attendant benefits over prior art apparatus. Likewise, the term greater than limit is to be construed as less than a negative directional limit when the component being monitored is decreasing (such as with $CO_2$ during a lean-roll condition).

Having thus described our invention, we claim:

1. Improved engine exhaust gas analysis apparatus comprising:

a. means for sampling the exhaust gases including means for generating a first signal indicating the amount of a component present in the exhaust gases;

b. differentiating means connected to said sampling means and including means responsive to said first signal for generating a second signal indicating the rate of change of said first signal with respect to time;

c. means connected to said differentiating means for comparing said second signal to a limit; and, d. means connected to said comparing means for indicating when said second signal exceeds said limit.

2. Improved engine exhaust gas analysis apparatus as claimed in claim 1 wherein:
said component in the exhaust gases is oxygen.

3. Improved engine exhaust gas analysis apparatus as claimed in claim 1 and comprising additionally:
means for setting said limit connected to said comparing means.

4. Improved engine exhaust gas analysis apparatus comprising:
 a. means for detecting a specific component of the exhaust gases;
 b. first circuit means connected to said detecting means for producing an output indicating the percent of said component;
 c. second circuit means connected to said output of said first circuit means for producing an output indicating the rate-of-change with respect to time of said component;
 d. means connected to said output of said second circuit means for comparing the instantaneous value of said output to a limit value; and,
 e. alarm means connected to said limit comparing means for indicating an alarm condition when said output of said second circuit means exceeds said limit value.

5. Improved engine exhaust gas analysis apparatus as claimed in claim 4 wherein:
said specific component is oxygen.

6. Improved engine exhaust gas analysis apparatus as claimed in claim 4 and comprising additionally:
means for setting said limit connected to said limit comparing means.

7. Improved engine exhaust gas analysis apparatus comprising:
 a. an oxygen sensor adapted to sample exhaust gases of an internal combustion engine:
 b. amplifier means connected to said sensor for producing an output indicating the percent of oxygen in said exhaust gases;
 c. differentiating means connected to said amplifier means for producing an output indicating the rate of change of said percent of oxygen output with respect to time;
 d. means connected to said differentiating means for comparing said rate of change to a limit; and,
 e. alarm means connected to said comparing means for signaling when said rate of change is greater than said limit.

8. Improved engine exhaust gas analysis apparatus as claimed in claim 7 and additionally:
means for setting said limit connected to said limit comparing means.

9. The method of detecting a lean-roll condition in an internal combustion engine comprising the steps of:
 a. sampling the exhaust gases from the engine to produce a first signal indicative of the percent of oxygen contained therein;
 b. differentiating said first signal to produce a second signal indicative of the time rate of change of said first signal;
 c. comparing said second signal to a limit value such that if said second signal exceeds said limit value the engine is in a lean-roll condition; and,
 d. activating means for indicating a lean-roll condition when said second signal exceeds said limit value.

10. An improved method of setting the idle mixture adjustment on the carburetor of an internal combustion engine comprising the steps of:
 a. sampliing the exhaust gases from the engine to produce a first signal indicative of the percent of oxygen contained therein;
 b. differentiating said first signal to produce a second signal indicative of the time rate of change of said first signal;
 c. comparing said second signal to a limit value such that if said second signal exceeds said limit value the engine is in a lean-roll condition;
 d. activating alarm means to indicate a lean-roll condition when said second signal exceeds said limit value;
 e. adjusting the dwell and timing of the ignition system of the engine to within specifications and to produce the lowest rate of lean-roll alarms;
 f. opening the idle mixture screw(s) of the carburetor an amount sufficient to assure a rich mixture condition;
 g. closing one idle mixture screw to cause a leaner mixture until a lean-roll condition is alarmed;
 h. opening the idle mixture screw adjusted in step (g) an amount to provide a safety margin of richness in the mixture to prevent lean-roll; and,
 i. repeating steps (g) and (h) on any other idle mixture screws on the carburetor.

* * * * *